United States Patent
Cinquin et al.

(10) Patent No.: US 10,175,181 B2
(45) Date of Patent: Jan. 8, 2019

(54) X-RAY IMAGING SYSTEM ALLOWING THE CORRECTION OF THE SCATTER RADIATION AND PRECISE DETECTION OF THE DISTANCE BETWEEN THE SOURCE AND THE DETECTOR

(71) Applicants: UNIVERSITE GRENOBLE ALPES, Saint Martin d'Hères (FR); SURGIQUAL INSTITUTE, La Tronche (FR)

(72) Inventors: Philippe Cinquin, St. Nazaire les Eymes (FR); Laurent Desbat, La Tronche (FR); Yannick Grondin, Challes les Eaux (FR)

(73) Assignees: UNIVERSITE GRENOBLE ALPES, Saint Martin d'Heres (FR); SURGIQUAL INSTITUTE, La Tronche (FR)

( * ) Notice: Subject to any disclaimer, the term of this patent is extended or adjusted under 35 U.S.C. 154(b) by 173 days.

(21) Appl. No.: 15/326,872

(22) PCT Filed: Jul. 21, 2015

(86) PCT No.: PCT/EP2015/066619
§ 371 (c)(1),
(2) Date: Jan. 17, 2017

(87) PCT Pub. No.: WO2016/012435
PCT Pub. Date: Jan. 28, 2016

(65) Prior Publication Data
US 2017/0205360 A1    Jul. 20, 2017

(30) Foreign Application Priority Data

Jul. 22, 2014  (FR) .................................... 14 57067

(51) Int. Cl.
*A61B 6/00*       (2006.01)
*G01N 23/04*    (2018.01)
(Continued)

(52) U.S. Cl.
CPC ............... *G01N 23/04* (2013.01); *A61B 6/06* (2013.01); *A61B 6/4035* (2013.01);
(Continued)

(58) Field of Classification Search
CPC .......... A61B 6/06; A61B 6/4035; A61B 6/582
See application file for complete search history.

(56) References Cited

U.S. PATENT DOCUMENTS 6,104,777 A    8/2000  Darboux et al.
6,490,475 B1  12/2002  Seeley et al.
(Continued)

FOREIGN PATENT DOCUMENTS

FR    2 759 800 A1    8/1998

OTHER PUBLICATIONS

Hao Yan, et al, "Projection Correlation Based View Interpolation for Cone Beam CT: Primary Fluence Restoration in Scatter Measurement with a Moving Beam Stop Array", IOP Publishing, Physics in Medicine and Biology, pp. 6353-6375, Oct. 12, 2010.
(Continued)

*Primary Examiner* — Dani Fox
(74) *Attorney, Agent, or Firm* — Pearne & Gordon LLP

(57) ABSTRACT

The invention relates to an X-ray imaging system wherein images are obtained using an X-ray blocking element, the system comprising means for determining a position of the detector (40) on the basis of coordinates of projected patterns of the blocker (20, 220) in an image in order to
(Continued)

especially be able to perform a calibration and/or correct the contribution of the scatter radiation in a radiographic image obtained by the system.

12 Claims, 9 Drawing Sheets

(51) Int. Cl.
G06T 11/00 (2006.01)
G21K 1/02 (2006.01)
A61B 6/06 (2006.01)

(52) U.S. Cl.
CPC ......... *A61B 6/4441* (2013.01); *A61B 6/5282* (2013.01); *A61B 6/582* (2013.01); *G06T 11/005* (2013.01); *G21K 1/025* (2013.01); *G01N 2223/303* (2013.01)

(56) References Cited

U.S. PATENT DOCUMENTS

| | | | |
|---|---|---|---|
| 7,486,773 B2 | 2/2009 | Maltz et al. | |
| 7,497,621 B2 | 3/2009 | Yatesenko et al. | |
| 7,551,716 B2 | 6/2009 | Rühmschopf | |
| 8,144,829 B2 | 3/2012 | Zhu et al. | |
| 2012/0207370 A1* | 8/2012 | Fahimian | A61B 6/032 382/131 |

OTHER PUBLICATIONS

So Hyun Ahn, et al., "Development of a Beam Stop Array System with Dual Scan Mode for Scatter Correction of Cone-Beam CT", Journal of the Korean Physical Society, vol. 64, No. 8, pp. 1220-1229, May 7, 2014.
M. J. Daly, et al,: "Geometric Calibration of a Mobile C-Arm for Intraoperative Cone-Beam CT", Medical Physics, vol. 35, No. 5, pp. 2124-2136, May 2008.
Xue Dong, et al., "Low-Dose and Scatter-Free Cone-Beam CT Imaging Using a Stationary Beam Blocker in a Single Scan: Phantom Studies", Computational and Mathematical Methods in Medicine, vol. 2013, Article ID 637614, pp. 1-8, Oct. 15, 2013.
Ho Lee, et al.: "Scatter Correction in Cone-Beam CT Via a Half Beam Blocker Technique Allowing Simultaneous Acquisition of Scatter and Image Information", Medical Physics, vol. 39, No. 5, pp. 2386-2395, May 2012.
Thomas M. Lehmann, et al,: "Survey: Interpolation Methods in Medical Image Processing", IEEE Transaction on Medical Imaging, vol. 18 No. 11, pp. 1049-1075, Nov. 11, 1999.
Y. Levakhina, "Where are We Today: Tomosynthesis Research and Development", Three-Dimensional Digital Tomosynthesis, Aktuelle Forschung Medizintechnik, 2014.
L. Alan Love, et al, "Scatter Estimation for a Digital Radiographic System Using Convolution Filtering", Department of Radiology/ Medical Physics, vol. 14, No. 2, pp. 178-185, Aug. 15, 1986.
Ruola Ning, et al, "X-Ray Scatter Correction Algorithm for Cone Beam CT imaging", Medical Physics, vol. 31, No. 5, pp. 1195-1202, May 2004.
Luo Ouyang, et al, "A Moving Blocker System for Cone-Beam Computed Tomography Scatter Correction", Medical Physics, vol. 40, No. 7, pp. 071903-1-071903-9, Jul. 2013.
Karsten Schorner, et al, "Scatter Correction Method by Temporal Primary Modulation in X-Ray CT", IEEE Transactions on Nuclear Science, vol. 59, No. 6, pp. 3278-3285, Dec. 1, 2012.
Jing Wang, et al, "Scatter Correction for Cone-Beam Computed Tomography Using Moving Blocker Strips: A Preliminary Study", Medical Physics, vol. 37, No. 11, pp. 5792-5800, Nov. 2010.
Lei Zhu, et al, "X-Ray Scatter Correction for Cone-Beam CT Using Moving Blocker Array", Medical Imaging 2005: Physics of Medical Imaging, Proceedings of SPEI, vol. 5747, pp. 251-258, 2005.
French Search Report issued in Patent Application No. FR 1457067 dated Jan. 13, 2015.
International Search Report issued in Patent Application No. PCT/ EP2015/066619 dated Sep. 23, 2015.
Written Opinion issued in Patent Application No. PCT/EP2015/ 066619 dated Sep. 23, 2015.
Jason Denton, Ph.D., "Two Dimensional Projective Point Matching", Dissertation, Jul. 1, 2002.
Richard Hartley, et al., "Multiple View Geometry in Computer Vision", Cambridge University Press, New York, Second Edition, pp. 1-673, (2000).
B. Spencer, et al., "On-line C-arm Intrinsic Calibration: Simulation Study", IEEE Medical imaging conference 2014.

* cited by examiner

X-RAY IMAGING SYSTEM ALLOWING THE CORRECTION OF THE SCATTER RADIATION AND PRECISE DETECTION OF THE DISTANCE BETWEEN THE SOURCE AND THE DETECTOR

TECHNICAL FIELD AND PRIOR ART

The present invention relates to the field of digital X-ray imaging.

In X-ray imaging, it is discriminated in the detected radiation, a direct radiation P called a "primary radiation" and a radiation S called a "secondary radiation" or still a "scattered radiation" and which mainly comes from the Compton effect scattering. In the case of conventional and interventional radiology, the S/P ratio can be higher than 5, whereas in mammography, this ratio is commonly located between 0.3 and 1.5.

The normalized contrast Cs of an image in the presence of a scattered radiation can be expressed as a function of a normalized contrast Cp of an image only consisting of a primary radiation P by the following relationship:

$$C_S = \frac{C_P}{1 + \frac{S^*}{P}}$$

Thus, the secondary radiation significantly degrades the contrast of the radiologic image.

Therefore, its contribution is generally intended to be reduced as much as possible.

For this, a solution consists in providing an anti-diffusing grid disposed between a detector also called an imager and a target object, for example a patient, a radiography of which is desired to be obtained.

This anti-diffusion grid enables the S/P ratio to be reduced but its drawback is to decrease the contribution of the primary radiation P at the same time.

To reach a signal to noise level in the image identical to that of a system without an anti-diffusion grid, it is thereby generally necessary to increase the exposure time or radiation intensity. As a result, there is an increase in the radiation dose to the patient by a factor that can be between 2 and 8 with respect to that employed in conventional radiology without using a grid An alternative way to correct the contribution of the secondary radiation consists in forming a digital processing on the image obtained.

Documents FR 2°759°800 and U.S. Pat. No. 7,551,716 give exemplary methods for digitally processing a radiographic image.

Image processing methods using a pre-recorded 3D model of the target object are efficient for applications, such as mammography, where the shape varies relatively little from one target object to the other. For other applications such as the conventional radiology, these methods are more difficult to implement and are likely to involve intensive calculations which results in a significant processing time.

In addition to artefacts due to the scattered radiation, images obtained by an X-ray imaging system can suffer from a second type of artefacts due to a variation in the position of the detector with respect to the source.

Such artefacts appear in particular in 3D imaging systems such as C-arm type systems.

Thereby, it may be important to be able to perform a calibration of these systems in order to be able to correct this second type of artefacts.

Calibration methods using inertial sensors in order to follow the real movement of the different components of the imaging system are known.

Their drawback mainly resides in the lack of reliability of the sensors which can be subject to disturbances.

An alternative calibration method using radiopaque markers is described for example in document U.S. Pat. No. 6,490,475.

With such a method, the image of the markers interferes with the image of the object the image of which is desired to be acquired.

Document "On-line C-arm Intrinsic Calibration: Simulation Study", by B. Spencer & L. Desbat, IEEE Medical imaging conference 2014, sets out another calibration method using this time 4 opaque markers linked to the source.

Document U.S. Pat. No. 7,497,621 provides as for it a calibration method using a radio-transparent grid. Such a method can, in some cases, lack accuracy in as much as it requires the detection of the pattern corresponding to a radio-transparent object in an image that can lack contrast.

There is a need to find a new X-ray imaging method for acquiring image(s), and a new planar X-ray imaging system improved relative to abovementioned drawbacks.

In particular, there is a need to implement a device which can enable both an accurate calibration of an X-radiation imaging system as well as a correction of the scattered radiation to be performed in a radiographic image.

DISCLOSURE OF THE INVENTION

One embodiment of the invention provides an X-ray imaging system provided with a device comprising:
  a blocking element intended to be disposed between an X-ray source and a target object an image of which is desired to be obtained, the blocking element being formed alternately by one or more opaque zones enabling X-rays to be blocked and one or more transparent zones enabling X-rays to pass therethrough,
  blocking element moving means configured to move the blocking element between at least one first position and at least one second position,
  the device being configured such that:
  in the first position, an opaque zone fully occupies a first given location and a transparent zone fully occupies a second given location,
  in the second position, the first given location is fully occupied by a transparent zone, the second location being fully occupied by an opaque zone.

The planar X-ray imaging system further comprises:
  an X-ray source,
  an X-ray detector,
  image acquiring means configured to perform a first acquisition of a first image frame or first image when the blocking element is in the first position and to perform a second acquisition of a second image frame or second image when the blocking element is in the second position.

The X-ray imaging system further comprises an image processing unit configured to determine a position of the detector from coordinates of one or more projected patterns of the blocker in the first image and/or in the second image.

With such a blocker, contrasted information-rich images are obtained which enables the position of the detector to be accurately determined.

This determination is important both to be able to calibrate the imaging system and to be able to perform a correction of the contribution of the scattered radiation in an image.

According to a possible implementation, the image processing unit includes or is coupled with a memory to store parameters of a first geometric transformation matrix relating coordinates of reference patterns with the coordinates of elements of the blocker respectively, each reference pattern corresponding to a projection of an element of the blocker in a radiographic image called a "reference" image generated when the detector is located at a reference distance from the source whereas the blocker is located in a given position from said first and second positions.

The reference position of the detector preferably corresponds to the position which is used by the image reconstruction algorithm. In other words, the reference position is the nominal position to perform the image reconstruction.

A reference image is an image including patterns of the blocker and which is acquired without a target object or intermediate object between the blocker and the detector.

The image processing unit can be thereby further configured to:
identify projected patterns of elements of the blocker in another radiographic image called an alignment radiographic image generated when the blocker is in the given position with respect to the detector, and to match the projected patterns in the alignment image with respectively elements of the blocker,
calculate parameters of a second geometric transformation matrix relating the coordinates of patterns projected in the alignment radiographic image with the coordinates of the reference patterns, and calculate the position of the detector from the parameters of the first and second matrices.

An alignment image can be acquired this time when a target object is located between the blocker and the detector. This target object can be for example a patient when the imaging system is dedicated to medical imaging.

One embodiment of the present invention also provides a method for calibrating a radiographic imaging system as defined above and comprising the following steps of:
disposing the blocker between the source and the detector,
acquiring by the detector at least one radiographic image, a so called alignment image, including one or more projected patterns of the blocker,
determining coordinates of projected patterns of the blocker in the alignment image and
calculating a position of the detector from coordinates of the projected patterns in the alignment radiographic image.

The method can further comprise a step of forming, using computing processing means, a corrected image of the target object.

For this, the primary radiation of at least one given pixel of the detector can be estimated depending on whether it belongs to a first pixel category or a second pixel category, belonging to the first or the second category depending on a predetermined criterion $q_1-q_2$ unique to each pixel and which can have been estimated beforehand, with $q_1, q_2$ being predetermined parameters representative of primary radiation fractions received by the given pixel of the detector in the first position of the blocker and in the second position of the blocker respectively.

Thereby, a first pixel category for which the criterion $q_1-q_2$ is different from 0 or higher than a given threshold z can be discriminated.

For a given pixel n belonging to this first category, the estimation $\hat{P}$ of the primary radiation received by the given pixel n, can depend on a ratio between:
a difference $I_1(n)-I_2(n)$ between a radiation intensity $I_1(n)$ detected by the given pixel n during the first acquisition and a radiation intensity $I_2(n)$ detected by the pixel n during the second acquisition,
a difference $q_1(n)-q_2(n)$.

A second pixel category for which the criterion $q_1-q_2$ is equal to 0 or lower than a given threshold z can be discriminated.

In this case, for a pixel m belonging to the second category, the estimation $\hat{P}(m)$ of the primary radiation received by the pixel m, can be a function of a primary radiation intensity $I_1(m)$ detected by the pixel m during the first acquisition of a primary radiation intensity $I_2(m)$ detected by the pixel m during the second acquisition, and of $\hat{S}int(n)$ a value estimated by interpolating the scattered radiation of the pixel m from a scattered radiation value calculated for its neighbouring pixels.

The criterion $q_1-q_2$ can be determined beforehand upon acquiring image frames, by performing a calibration during which a first acquisition of a first image frame and then a second acquisition of a second image frame, all of which are in a device without a target object, are performed.

In order to make the image of the target object, the criterion $q_1-q_2$ for a given pixel can be deduced as a function of localization of this given pixel with respect to the blocker in the first position and in the second position.

To perform this localization, the positioning of the blocker can be estimated relative to the detector by analysing one of the image frames, for example the first frame. The accurate knowledge of the positioning of the detector can thus also be used in order to correct the contribution of the scattered radiation.

For a given pixel, a value of $q_1-q_2$ can be extracted from a pre-recorded calibration file or estimated by calculation.

According to another aspect of the present invention, in the case where the system is a planar imaging system adapted to perform a two dimension image acquisition, the system can be configured such that the source, blocking element and imager have during the first acquisition a first arrangement and during the second acquisition a second arrangement different from the first arrangement, the positioning of the source and of the detector with respect to the target object or to a support on which the target object lies, being the same in the first arrangement and the second arrangement.

Thus, a particular embodiment of the present invention also provides an X-ray imaging method for acquiring image(s) in 2 dimensions.

This method comprises steps of:
performing a first acquisition of a first image frame of a target object using a detector provided with a plurality of pixels, by exposing the target object to an X-ray source, a blocking element being disposed between the source and the target object, the blocking element being formed alternately by one or more opaque zones enabling X-rays to be blocked and one or more transparent zones enabling X-rays to pass therethrough, the source, blocking element, and detector having during the first acquisition a first arrangement in which the blocking element has a first position with respect to the detector, moving the blocking element with respect to the detector, such that the blocking element moves from the first position to a second position with respect to the detector, and then, performing a second acquisition of a second image frame of the target object by exposing the target object to the X-ray source, the source, blocking element, and detector having during the second acquisition a second arrangement different from the first arrangement and in which the blocking element is in the second position.

The positioning of the source and of the detector with respect to the target object or to a support on which the target object lies, can as for it be the same and be kept between the first arrangement and the second arrangement.

In such a system, the blocking element is likely to assume a first position and a second position enabling complementary image frames to be acquired.

For this, the first position and the second position of the blocking element can be provided such that:

in the first position, an opaque zone of the blocking element occupies a first location in a given perimeter through which an X-ray beam from the source is intended to pass and a transparent zone of the blocking element occupies a second location in the given perimeter, in the second position, the first location and the second location are respectively occupied by a transparent zone and an opaque zone of the blocking element.

According to a possible implementation, the blocking element, the first position of the blocker and the second position of the blocker can be provided such that: in the first position, an opaque zone of the blocking element occupies a first location symmetrical to that occupied by another opaque zone of the blocking element in the second position, with respect to a plane passing through the source and which is orthogonal to a front face of the blocker.

According to a possible implementation, the first position and the second position of the blocking element are provided such that:

in the first position, at least one first pixel of the detector is disposed in the shadow or penumbra of the blocking element whereas at least one second pixel is directly illuminated by the X-ray source, in the second position, the second pixel is located in the shadow of the blocking element whereas the first pixel is directly illuminated when in the first position, it is located in the shadow or it is located in the penumbra of the blocking element when in the first position, it is in the penumbra of the blocking element.

In this case, a third pixel disposed on the detector such that the second pixel is located between the first pixel and this third pixel, can be located:

in the shadow of the blocking element when the blocking element is in the first position, directly illuminated by the X-ray source when the blocking element is in the second position.

According to a first possible implementation, the acquisition of the first image frame can be performed by exposure to a first x-radiation pulse emitted by the source, whereas the second acquisition is performed by a second exposure to a second X-radiation pulse emitted by the X-ray source, the X-ray source being OFF or emitting no radiation between the first and the second pulse.

According to a second possible implementation, the acquisition of the first image frame is performed by exposing the target object to an X-radiation pulse emitted by the source, whereas the acquisition of the second image frame is performed by exposing the target object to this same X-radiation pulse, the blocking element being thereby mobile for the duration of this pulse.

According to a possible implementation, the movement of the blocking element between the first position and the second position is made by translating the blocking element by a given pitch p and in a plane parallel to the detector.

This translation pitch p can be equal to k*l, with k being an integer, l being the width of opaque zones of the blocking element.

According to a possible implementation of the blocking element, the latter can be provided with a front face alternately including opaque zones and transparent zones parallel to each other.

Alternatively, a blocking element the front face of which includes opaque zones and transparent zones having a checkerboard arrangement can be provided.

According to another alternative implementation, the movement of the blocking element between the first and the second position can be made by rotating the blocking element about an axis passing through the X-ray source.

In this case, the blocking element can have a curved profile.

In one alternative, the blocker consists of opaque and transparent zones forming an arc of a circle the centre of which is the X-ray source.

According to another aspect of the invention, an imaging device configured for the implementation of a method as defined above is provided.

BRIEF DESCRIPTION OF THE DRAWINGS

The present invention will be better understood upon reading the description of exemplary embodiments given by way of purely indicating and in no way limiting purposes, making reference to the appended drawings in which.

Identical, similar or equivalent parts of the different figures bear the same reference numerals so as to facilitate switching from one figure to the other.

Different parts represented in the figures are not necessary drawn to a uniform scale, for making the figures more understandable.

DETAILED DISCLOSURE OF PARTICULAR EMBODIMENTS

Figure 1:
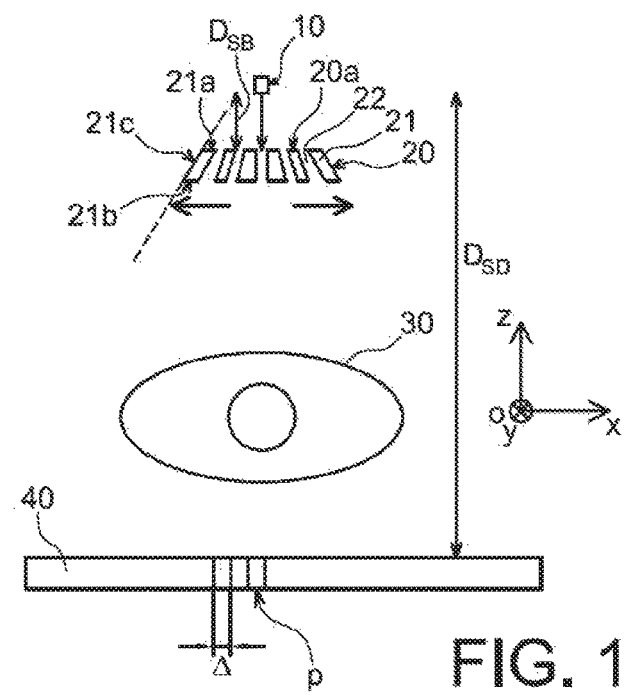
FIG. 1 illustrates an exemplary X-ray planar imaging system provided with an X-ray blocking element movable between several positions for acquiring image frames.

An exemplary embodiment of an X-ray planar imaging system is illustrated in FIG. 1.

Such a system can be applied for example to mammography, or to conventional and/or interventional radiology (fluoroscopy) and enables several image frames to be acquired in order to form an image of a target object 30 or of a region of this target object 30, the target object 30 being for example a patient, possibly placed on a support (not represented).

The image frames of the target object 30 are produced using a digital detector 40, formed by a plurality of detection elements also called "pixels", which are arranged as a matrix.

In order to correct the scattered radiation on the image of the target object 30, the system includes a blocking element 20 arranged between an X-ray source 10 and the target object 30, the latter being itself placed between the blocking element 20 and the detector 40. An image frame is an image obtained in a given position of the blocker.

The blocking element 20 is formed alternately by X-ray opaque zones 21, that is they do not or hardly let X-rays pass, and X-ray transparent zones 22. The opaque zones 21 are based on a material having a high X-ray absorption power such as for example lead or tungsten.

By way of indicating purposes, at energies used in conventional radiology, zones having a thickness of several millimeters based on lead are opaque to X-rays. At 60 keV for example, the transmission factor of 3 mm lead zones is for example in the order of $2*10^{-7}$.

The transparent zones 22 can be in the form of empty slots based on a very low X-ray absorbing material, such as for example carbon.

The opaque zones 21 can be in the form of parallelepiped blocks including side faces 21c connecting a front face 21a disposed facing the X-ray source, a back face 21b disposed facing the target object and the detector 40, the side faces 21c being tilted with respect to each other and oriented along different respective directions focused to the source 10, in other words which converge to the X-ray source.

In the exemplary embodiment illustrated in FIG. 1, the device shown in a top view, includes a trapezoidal shaped blocker 20, having a front face 20a disposed facing the X-ray source, this front face 20a being of a smaller cross-section area than that of its back face 20b opposite the front face 20a and disposed facing the target object 30 and the detector 40.

Figure 2:
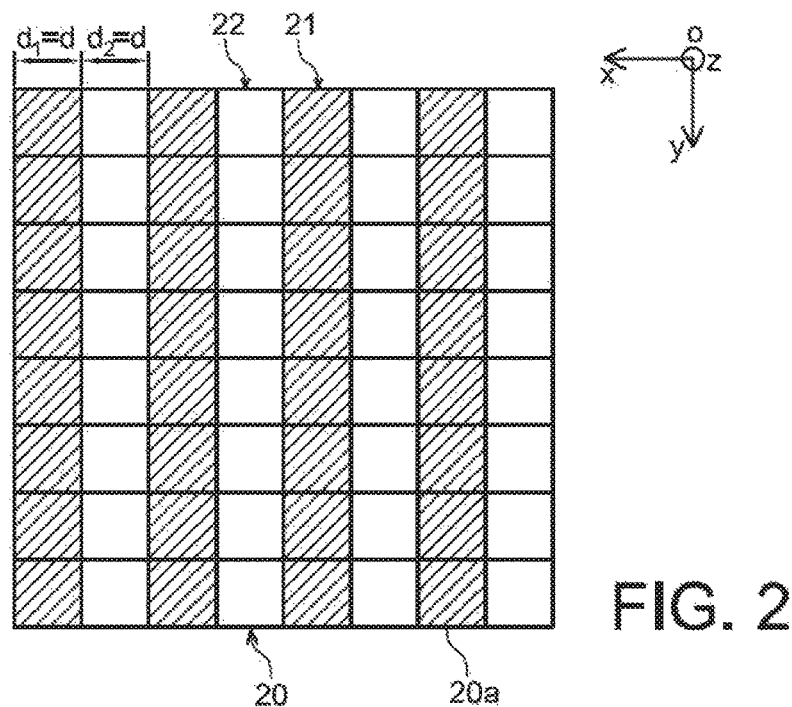
FIG. 2 illustrates a particular exemplary arrangement of transparent zones and opaque zones at a front face of an X-ray blocking element.

An exemplary particular arrangement of the front face 20a of the blocker 20 is illustrated in FIG. 2. The transparent zones 22 have in this example a rectangular shape similar to that of the opaque zones 21, the transparent zones 22 having widths (measured in a direction parallel to the plane [0; x; y] of the orthogonal reference frame [0; x; y; z]) equal to d, with d that can be for example between 0.2 and 5 mm. The 0.2 mm value can correspond to the order of magnitude of the size Δ=0.2 mm of a pixel, the 5 mm value corresponding to several tens of times the size of a pixel.

A blocker 20 with opaque zones with a low width d enables the scattered radiation to be better estimated whereas a blocker provided with opaque zones with a higher width d enables the penumbra part to be reduced with respect to the shadow part in the acquired image frame. A blocker can thus be provided by making a compromise between both these criteria.

With such an imaging system, an acquisition of several image frames is made, each of these image frames can be obtained in a different position of the blocking element 20.

The blocking element 20 is thus caused to be moved between several positions, this movement being, in the exemplary particular embodiment illustrated in FIG. 1, a translation, preferably along a plane parallel to the main plane of the detector (i.e. a plane passing through the detector and parallel to the plane [0; x; z] on the device of FIG. 1).

Figure 3:
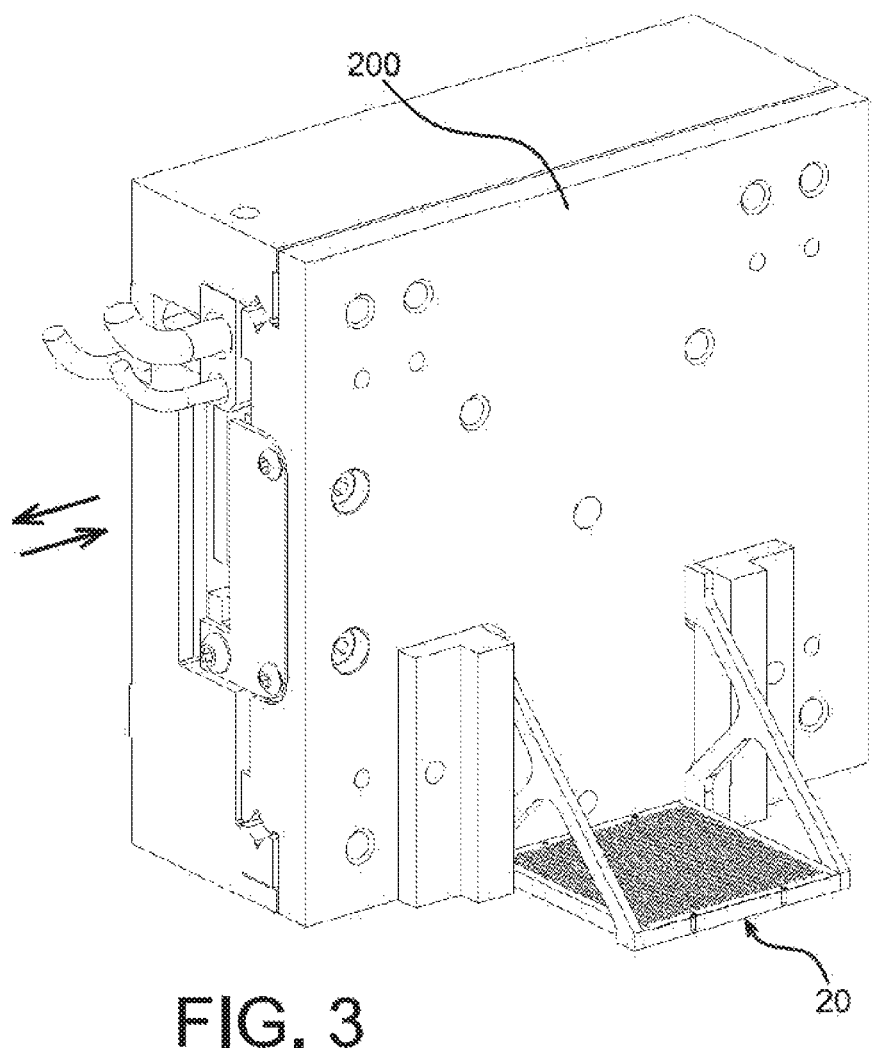
FIG. 3 illustrates an exemplary device configured to move an X-ray blocking element.

The translation can be made via a motorized moving device, for example a single axis linear positioning table 200 such as that illustrated for example in FIG. 3, and on which the blocker 20 is attached.

The positioning table 200 and blocker 20 assembly can be mounted with the source 10 and integrated on the radiologic tube (not represented).

The translation movement of the blocking element 20 is made between two acquisitions of successive image frames, at a given pitch p in a given direction belonging to a plane parallel to the main plane of the detector 40, with p the translation pitch which can be equal to k*d, k being a non-zero integer, d being the width of the opaque zones 21 of the blocker viewed from the source 10.

Upon acquiring the image frames and between two successive acquisitions, the positioning of the source 10 and of the detector 40 with respect to the target object 30 or to a support on which the target object 30 lies, remains the same. Thus, preferably, only the blocking element 20 moves to carry out the different acquisitions of image frames.

The front face 20a of the blocking element 20 can be located at a distance DSB for example between 5 cm and 20 cm from the X-ray source 10. The distance DSD between the X-ray source 10 and the detector 40 can be for example between 70 cm and 120 cm. These values are given by way of example to carry out a radiography.

The voltage applied to the electrodes of the X-ray tube can be similar to that of a conventional system, for example in the order of a few tens kV. For each image frame, the energy fluence delivered by the source 10 can be equal to that of a conventional imaging system not using a blocker or an anti-diffusion grid.

Figure 4A:
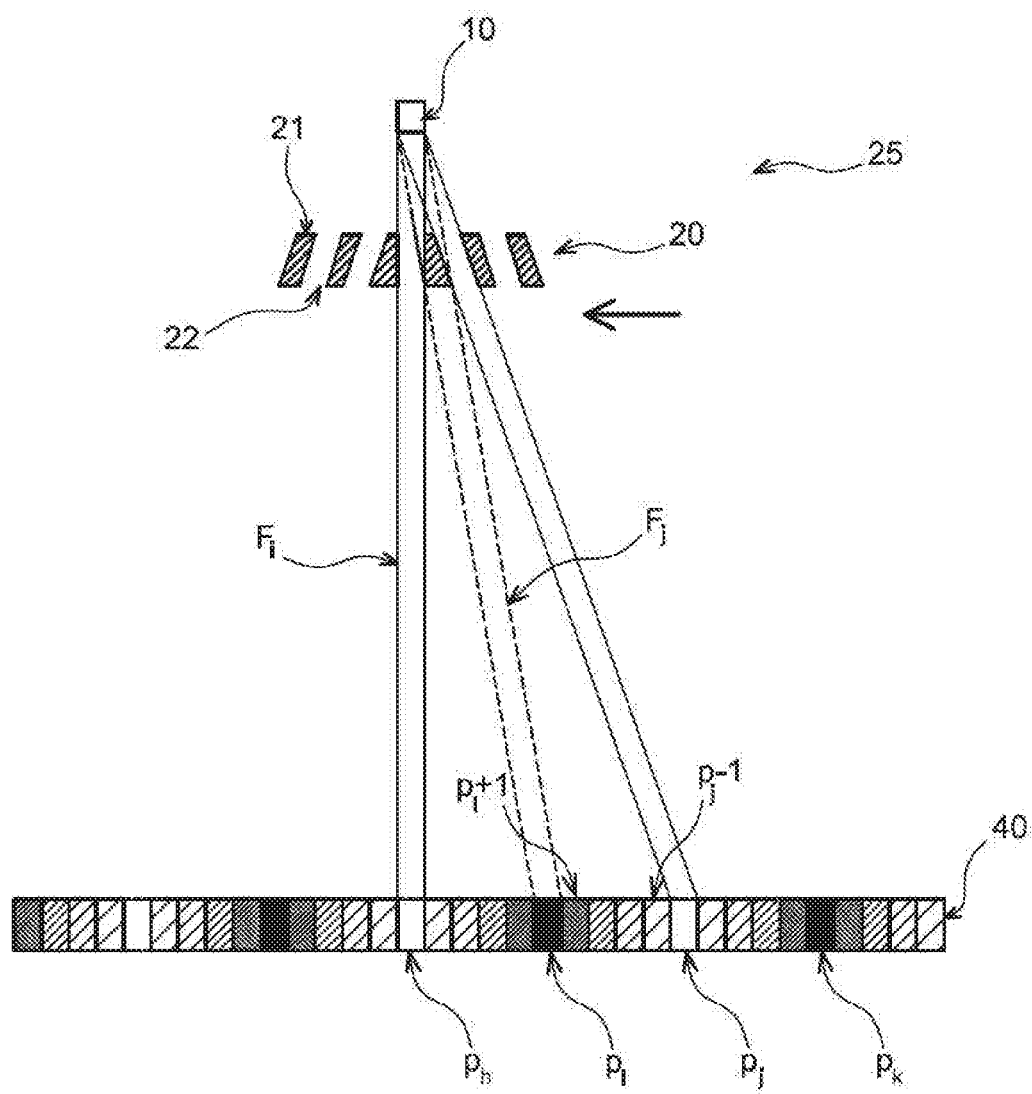
FIGS. 4A-4B and 5A-5B and 6 illustrate different positions of a blocker in a planar imaging system, switching of the blocker from one position to the other being performed in this example by translation.
Figure 4B:
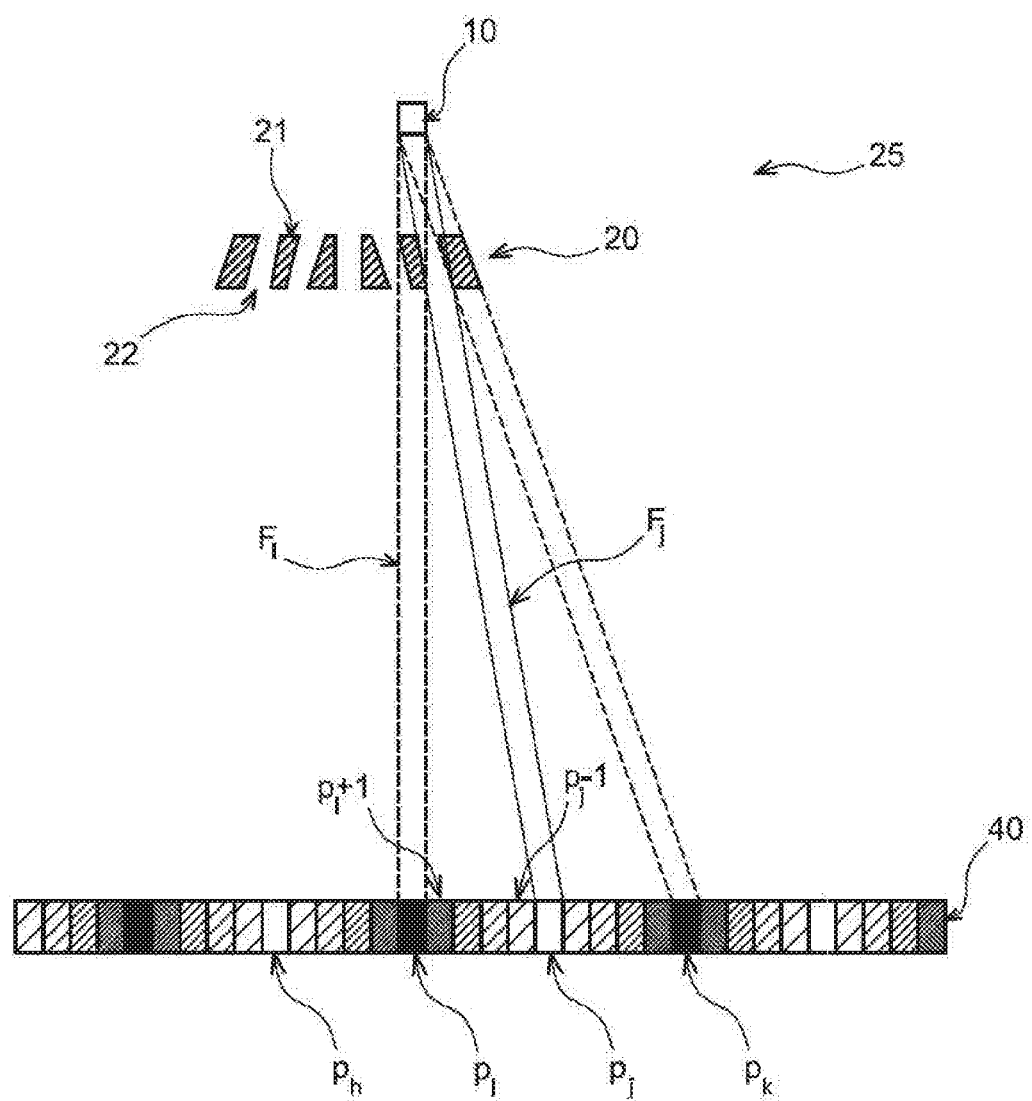
Figure 5A:
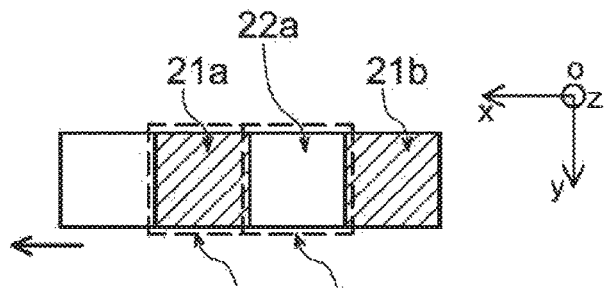
Figure 5B:
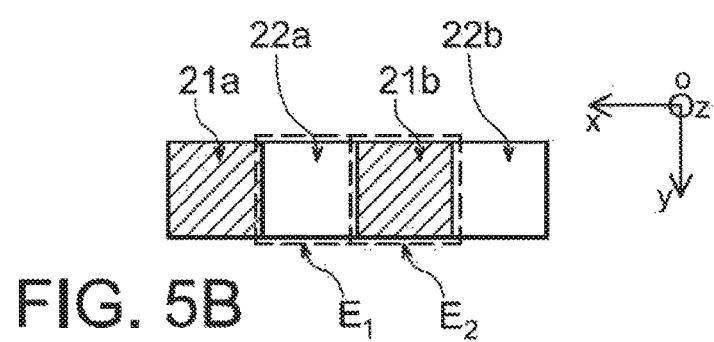

According to an embodiment illustrated in FIGS. 4A-4B and 5A-5B (FIGS. 5A-5B illustrating positions of the blocker front face viewed from the X-ray source), the acquisition of two complementary image frames can be provided with two different positions of the blocker 20, a first acquisition of a first image frame being made in a first position of the blocker 20 with respect to the detector 40 (FIGS. 4A and 5A), a second acquisition of a second image frame being made in a second position of the blocker 20 with respect to the detector 40 (FIGS. 4B and 5B).

The positioning of the source 10 and the detector 40 with respect to the target object 30 or to a support (not represented) on which the target object lies, does not vary between the first acquisition and the second acquisition.

Preferably, the source 10 and the detector 40 are stationary between two acquisitions of image frame. Preferably also, the target object 30, for example a patient, is also stationary between the first and the second acquisitions.

The positioning of the opaque zones 22 of the blocker 20 in the first position of the blocker is preferably provided complementary to that of the opaque zones 22 of the blocker 20 when it is in the second position.

Thus, in the first position of the blocker 20, an opaque zone 21a of the blocker 20 occupies a first location E1 in a given perimeter (perimeter 25 in FIGS. 2A and 2B) through which the X-ray beam from the source 10 passes whereas a transparent zone 22a of the blocker 20 occupies a second location E2 in the given perimeter (FIG. 5A).

In the second position, the first location E1 and the second location E2 are respectively occupied by the transparent zone 22a and an opaque zone 21b of the blocking element 20 (FIG. 5B).

Figure 6:
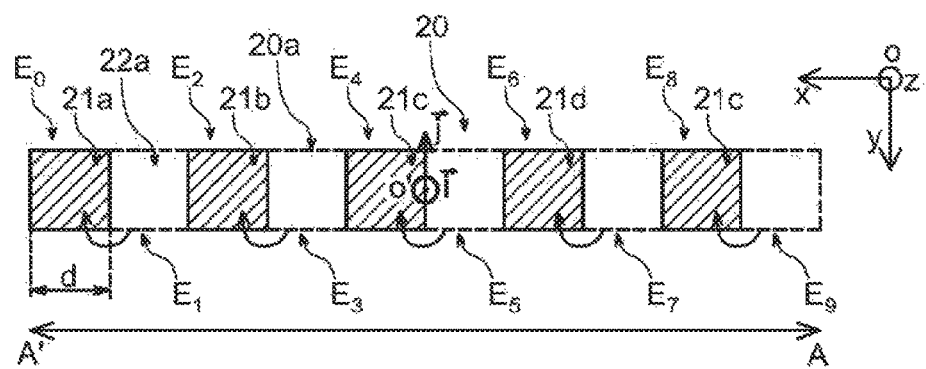

According to a possible particular implementation illustrated in FIG. 6, the blocker 20 and its movements can be advantageously provided such that the positioning of opaque zones in the first position of the blocker 20 includes a symmetry with the positioning of opaque zones in the second position of the blocker 20.

In the example of the FIG. 6, the front face 20a of the blocker 20 viewed from the X-ray source is shown in the second position of the blocker 20, i.e. after a translation movement at a pitch here for example equal to the width d of an opaque zone. In this figure, zones $E_1$, $E_3$, $E_5$, $E_7$, $E_9$ with dashed lines designate locations occupied before by the opaque zones 21a, 21b, 21c, 21d, 21e in the first position of the blocker 20.

Thus, locations $E_0$, $E_2$, $E_4$, $E_6$, $E_8$ occupied by the opaque zones 21a, 21b, 21c, 21d, 21e of the blocker 20 in the second position are respectively symmetric with locations $E_9$, $E_7$, $E_5$, $E_3$, $E_1$ occupied by the opaque zones 21e, 21d, 21c, 21b, 21a in the first position, if it is considered a plane of symmetry [0'; i; j] (given in FIG. 6 and which is parallel to the plane [0; y; z] of the orthogonal reference frame [0; x; y; z]) orthogonal to the front face 20a of the blocker 20 and to a movement axis A'A of the blocker (the movement axis being parallel to the vector x of the orthogonal reference frame [0; x; y; z) and passing through the source 10 and the centre of the front face 20a of the blocker 20 between an opaque zone and a transparent zone.

As a result of these different positions of the blocking element 20, in the first position of the blocker 20, pixels pi, pk are directly illuminated by the X-ray source 10 whereas other pixels ph, pj, which are not neighbours of the pixels pi, pk are disposed in the shadow of the blocking element 20, the detector 40 including alternately directly illuminated pixels and pixels in the shadow with between an illuminated pixel pi and a pixel pj in the shadow, pixels $p_{i+1}$, ..., $p_{j-1}$, which are in different levels of penumbra and thus of intensity (FIG. 4A).

The movement of the blocking element 20 between the first position and the second position is provided such that in the second position (FIG. 4B), the pixels pi, pk are now in the shadow of the blocking element 20, whereas the other pixels ph, pj are directly illuminated by the X-ray source. The detector 40 thus also includes alternately directly illuminated pixels and pixels in the shadow with between an illuminated pixel pj and a pixel pi in the shadow, pixels $p_{i+1}$, ..., $p_{j-1}$, which are located in different levels of penumbra and thus of intensity. A particular processing of the pixels could be made which, among pixels $p_{i+1}$, ..., $p_{j-1}$, located in the penumbra in both positions, have an intensity (or penumbra level or grey level) equal or substantially equal or substantially equal between the first and the second position.

By "directly illuminated" pixel, it is meant here that part of the radiation beam X Fi propagating along a rectilinear direction from the source 10 to the detector 40 and reaching this pixel pi, does not meet an opaque zone 21 of the blocking element 20.

By "penumbra or shadow", it is meant that part of the radiation beam X Fj propagating along a rectilinear direction from the source 10 to the detector 40 and directed to a pixel pj located in the shadow or the penumbra, meets an opaque zone 21 of the blocking element 20, the shadow being a particular case of penumbra, for which the pixel pj is fully masked by an opaque zone 21 of the blocker and/or receives a zero amount or an amount that is considered negligible of photons. In the presence of a target object, the pixels in the shadow mainly receive scattered rays.

FIGS. 4A-4B illustrate a case, for example where the image is a grey-level digital image, the value of each pixel including intensity information ranging from black, for example with the value 0, reflecting the situation of a pixel in the shadow, to white, for example with a value 255, reflecting the situation of a directly illuminated pixel, the pixels in the penumbra being represented by different grey hues.

By pixels pi and pj "which are not neighbours", it is meant here that the pixels pi, pj are separated via one or more pixels $p_{i+1}$, ..., $p_{j-1}$ from the detector 40.

Because of the complementarity of both image frames, the total number of pixels which are directly illuminated for the whole of both image frames can be equal to the total number of pixels which are located in the shadow when the whole of both image frames is taken into account.

FIGS. 4A-4B are given by way of illustrating example with a given pixel size in which directly illuminated zones of the detector and zones of the detector which are in the shadow are individual pixels $P_h$, $p_i$, $p_j$, $p_k$.

Figure 7:
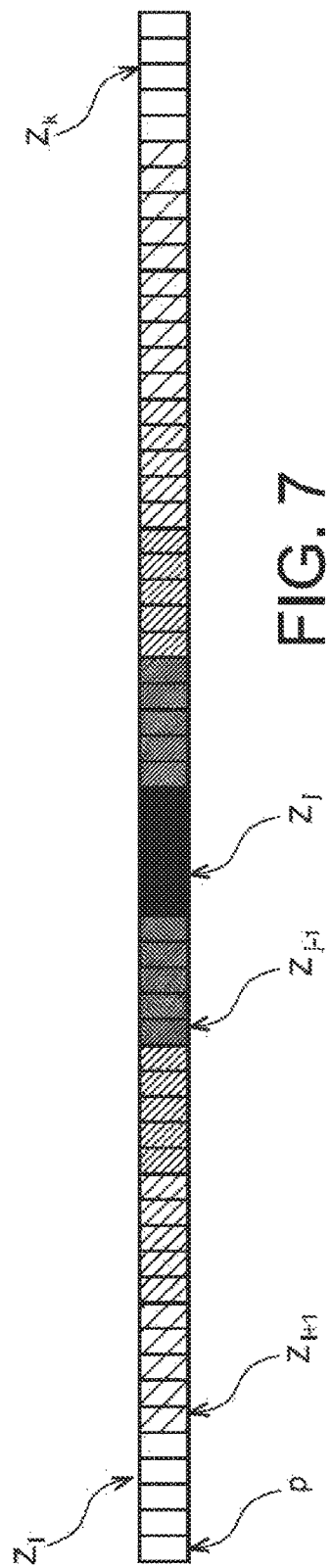
FIG. 7 illustrates an exemplary lighting of the pixels of a detector in an imaging system provided with a blocker.

However, the directly illuminated zones $Z_i$, $Z_k$ of the detector, the zones Zj of the detector which are in the shadow and the zones $Z_{i+1}$, ..., $Z_{j-1}$ can be as illustrated alternatively in FIG. 7, groups of neighbouring pixels p.

The acquisition of the first image frame and of the second image frame, complementary to the first frame, can be made, during an exposure of the detector 40 to an X-radiation pulse emitted by the source 10 during which the blocking element 20 moves.

Alternatively, a first exposure of the detector 40 can be made at a first X-radiation pulse emitted by the source 10 and then a second exposure to a second X-radiation pulse emitted by the source 10, the X-ray source being OFF or emitting no radiation between the first and the second pulses.

Since both positions of the blocking element 20 are complementary to make the acquisition of both frames, the detector 40 can be caused to receive a total dose equivalent to that of an acquisition without a blocking element. The signal to noise ratio on the raw image obtained can be equal to that of an image obtained via a system without a blocker.

In addition to the acquisition of image frames, prior to making an image from these frames, the position of the blocking element 20 relative to the detector 40 and its pixels could have been determined.

This determination can be made after acquiring the first image frame and/or the second image frame, and can be made by analysing the image frames themselves.

For this, the analysis by a computing module 50 or a unit 50 for processing the image frame can include a first step of detecting the patterns of the projection of the elements (opaque and/or transparent zones) of the blocker on the image characterized by alternate illuminated (strong signal intensity) zones (pixels) and non-illuminated (low signal intensity) zones. The boundaries of these zones which are lines can be accurately identified by calculation methods using the Fourier transform or the Hough transform, such as those set out in R. Szeliski, Computer Vision: algorithms and applications, Springer 2010.

From the detection in the image of patterns of the opaque zones of the blocker, it is then possible by applying a method such as those developed for camera calibration in the field of computer vision, for example a method such as described in R. I.

Hartley and A. Zisserman, Multiple View Geometry in Computer Vision, Cambridge University Press 2000, to determine the relative positions of the blocker and detector.

The choice of the method for localizing the blocking element 20 with respect to that of the detector 40 depends on the geometry of the latter.

A digital processing is then made to make the image from both complementary frames.

In this processing, one can consider:
the intensity $I_1$ of the radiation read in a given pixel n during the acquisition of the first image frame such as $I_1(n)=q_1(n)P(n)+S_1(n)$, with $q_1$ a predetermined factor unique to the pixel n, $P_1$ the primary radiation intensity received by the given pixel n during the first acquisition, $S_1$ the scattered radiation intensity received by the given pixel n during the first acquisition,
the intensity $I_2$ of the radiation read in the given pixel n, for the second image frame: $I_2(n)=q_2(n)P(n)+S_2(n)$, with $q_2$ a predetermined factor unique to the pixel n, $P_2$ the primary radiation intensity received by the pixel n during the second acquisition, $S_2$ the primary radiation intensity received by the pixel n during the second acquisition.

Terms $I_1(n)$ and $I_2(n)$ thus consist of a fraction of the primary radiation received by the pixel n, as well as the radiation which, because of scattering, reaches the pixel n.

For a pixel such as for example pixel pi in FIGS. 2A-2B directly illuminated during the acquisition of the first frame and located in the shadow during the acquisition of the second frame, $q_1=1$ and $q_2=0$ can be considered.

For other pixels pi+1, ..., pj−1 located in the penumbra, $q_1$ and $q_2$ ranging in the interval]0; 1[are considered.

For a pixel such as for example the pixel pj in FIGS. 2A-2B located in the shadow during the acquisition of the first frame and directly illuminated during the acquisition of the second frame, $q_1=0$ and $q_2=1$ can be considered.

For two positions of the blocking element 20 offset by a translation pitch equal to d, the following approximation can be made: $S_1 \approx S_2$ hypothesizing that there is a strong spatial correlation in the scattered radiation term.

Factors $q_1(n)$ and $q_2(n)$ are unique to the pixel n and represent fractions of the primary radiation received by the pixel n by taking geometric and physical penumbras in both positions of the blocking element 20 into account.

The following relationship: $q_1=1-q_2$ can be considered.

Estimations of the factors $q_1$ and $q_2$ can have been made beforehand for each pixel as soon as the system geometry is known, in particular the focus size of the X-radiation source 10, the width d of the opaque zones, the width $\Delta$ of the pixels, the source-detector distance DFI, the source-blocker distance DFB, and the relative position of each element, i.e. the focus of the X-ray source, the blocker 20 and the detector 40.

For example, the determination of the factors $q_1$ and $q_2$ can be made by digital simulation of an exposure of the detector to an X-radiation, without a target object, for different geometric configurations, i.e. different positions and orientations of the blocker with respect to the detector. In one alternative, $q_1$ and $q_2$ are determined by measurements without a target object for different geometric configurations. For each image or image frame Im_q1, Im_q2 obtained, the image is divided by the maximum value measured in a pixel: both image frames Im_q1, Im_q2 are thus normalized, such that the factors $q_1$ and $q_2$ are then between 0 and 1.

An estimation of the difference $q_1(n)-q_2(n)$ unique to each given pixel n can also have been made by performing under conditions similar to those previously described but without a target object: a first intensity measurement of the given pixel in the first position of the blocking element 20 and a second intensity measurement of the given pixel in the second position of the blocking element 20, the estimation of the factor $q_1-q_2$ then depending on the difference between both these measured intensities.

After these prior measurements, the values of the factor $q_1-q_2$ can be listed in a calibration file that can be queried afterwards when the processing aiming at making an image of a target object is carried out.

In this image making phase, to be able to associate with a given pixel n the proper pre-recorded factor $q_1(n)-q_2(n)$, the determination of the position of the blocker 20 with respect to the detector 40 that has been made by analysing one or more image frames Im_q1, Im_q2, for example the first frame Im_q1 is used.

Therefore, two pixel categories can be discriminated: a first pixel category for which $q_1-q_2 \neq 0$ or $|q1-q2|>z$ with z a predetermined threshold for example in the order of 0.5 and a second pixel category for which $q_1--q_2$ reaches a threshold close to 0 or equal to 0.

For a given pixel n, when for this pixel $q_1(n)-q_2(n) \neq 0$, it is considered that this given pixel n belongs to a first pixel category and a first estimator $\hat{P}$ of the primary radiation is used such as:

$$\hat{P}(n) = \frac{|I1(n) - I2(n)|}{|q1(n) - q2(n)|}$$

For a pixel m such as $|q1-q2| \leq z$ or equal to 0, it is considered that this pixel m belongs to a second pixel category and a second estimator $\hat{P}'$ of the primary radiation is used such as:

$$\hat{P}'(n)=I_1(n)+I_2(n)-(S_1(n)+S_2(n))$$

$\hat{P}'(n)=I_1(n)+I_2(n)-2\hat{S}_{int}(n)$, with $\hat{S}_{int}(n)$ a value estimated by interpolating the scattered radiation of the pixel m from a value of scattered radiation calculated for its neighbouring pixels and for which $|q_1-q_2| \neq 0$ ou>z.

To determine $\hat{S}_{int}(n)$, an interpolation method such as described for example in document "Survey: Interpolation Methods in Medical Image Processing, IEEE transactions on medical imaging, vol. 18, no 11, 1999 can be employed.

In the example of FIGS. 4A-4B, pixels located in the middle of a segment between pixel $p_i$ and pixel $p_j$ or between pixel $p_h$ and pixel pi or between pixel $p_j$ and pixel $p_k$ and the grey level of which varies very little or does not vary between both positions of the blocker, are likely to belong to the second category, that is that for which $|q_1-q_2| \leq z$ or equal to 0.

Then, after making the image a processing for example of the filtering type and aiming at reducing the noise can be made.

The above discussed computing processing module 50 enabling an image to be produced from the image frames generated by the detection device 40 can be provided with at least one processor, with at least one memory module and at least one input peripheral. The processor can be, for example, a microprocessor, an FPGA or a central processing unit, or a processor network.

The memory module can comprise, for example, a read only memory ROM, a program memory EPROM, a dynamic memory DRAM or any other RAM type memory, a magnetic or optical storage element, registers or other volatile and/or non-volatile memories.

Algorithms as instructions can be stored in the program memory, and enable the above described digital processing steps to be performed to make an image from complementary frames.

A program, enabling the digital processing method or a calibration method to be implemented can be residing or recorded on a medium for example a memory card SDRAM or a DVD-ROM or a Blu-ray disk or a removable hard disk or a magnetic medium or a USB key likely to be read by the computing processing module 50.

Figure 8:
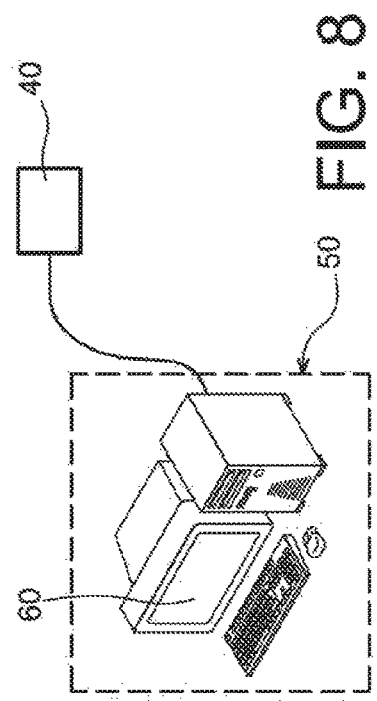
FIG. 8 illustrates an exemplary computing image processing module for making an image from complementary image frames or complementary images obtained in complementary positions of a blocking element.

The computing processing module 50 can also be connected to a peripheral such as for example a screen 60 enabling the radiographic image made (FIG. 8) to be displayed.

The computing processing module 50 can be connected to a network, possibly by a wireless communication.

Figure 9:
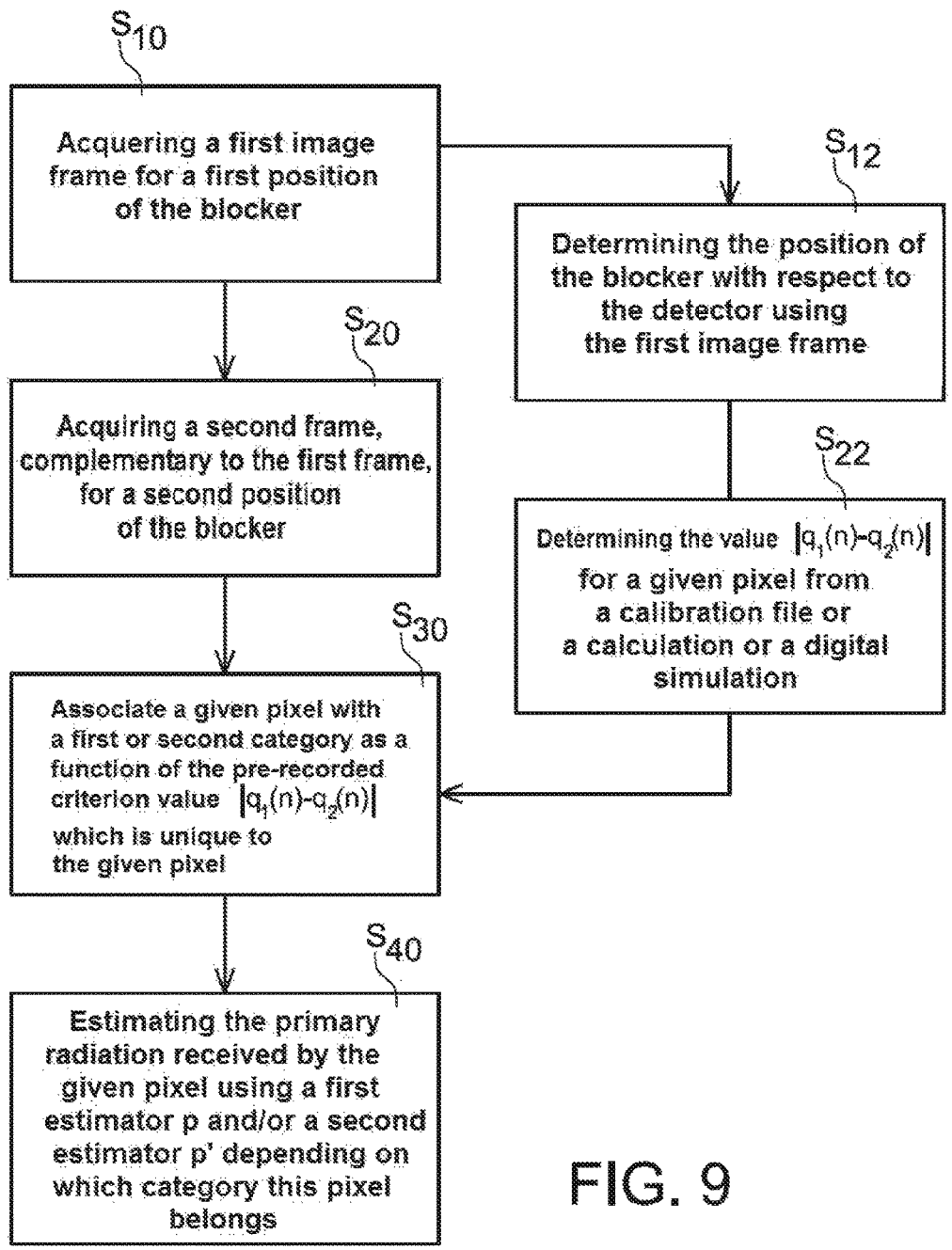
FIG. 9 illustrates an exemplary flowchart of a processing performed by a computing processing module to make an image from complementary image frames obtained in complementary positions of a blocking element.

An exemplary flowchart summarizing a series of processing steps likely to be made by the computing processing module 50 is given in FIG. 9.

A first step consists in acquiring a first image frame provided by the detector 40 for the first position of the blocking element 20 (step $S_{10}$).

Then, a determination of the position of the blocker with respect to the detector using this first frame is implemented (step $S_{12}$).

After the first acquisition, a second image frame provided by the detector 40 is acquired for the second position of the blocking element 20 (step $S_{20}$).

From these complementary image frames, an image is made by discriminating between pixels of a first pixel category for which $q_1-q_2 \neq 0$ or even $q_1-q_2$ higher than a threshold z and pixels of a second category for which $q_1-q_2=0$ or even $q_1-q_2$ lower than a threshold z (step $S_{30}$).

For this, from the knowledge of the positioning of the blocker 20 with respect to the detector 40, the value of $q_1-q_2$ could have been determined (step $S_{22}$) for each pixel from values recorded in a calibration file, the values of the calibration file can as for them result from prior measurements performed in the first and the second position of the blocker but without a target object.

Then, (step $S_{40}$) the primary radiation received for each pixel is estimated as a function of the category to which these pixels belong, wherein a first estimator $\hat{P}(n)$ can be used for the pixels of the first category whereas a second estimator $\hat{P}'(n)$ can be used for the second pixel category.

Figure 10:
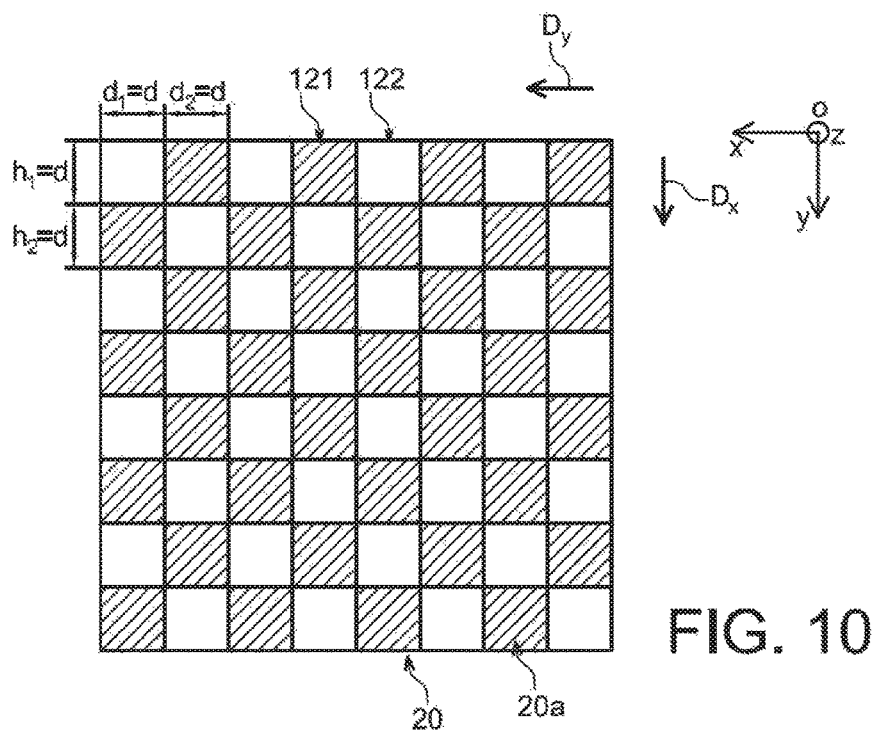
FIG. 10 illustrates another exemplary particular arrangement of transparent zones and opaque zones at a front face of an X-ray blocking element.

According to an alternative of the previously described imaging system, as illustrated for example in FIG. 10, a blocking element 120 with a different shape and in which opaque zones 121 and transparent zones 122 are distributed in two dimensions according to a checkerboard arrangement can be provided. The blocker 120 thus includes several rows, each including alternate opaque zones 121 and transparent zones with a square shape with a side d.

The movement of the blocker 120 can in this case be made by a translation along several directions Dx, Dy, parallel to the sides of the squares and at a pitch p=k*d with k an integer.

The exemplary embodiments just described provide a translation movement between the different positions for acquiring an image.

Figure 11:
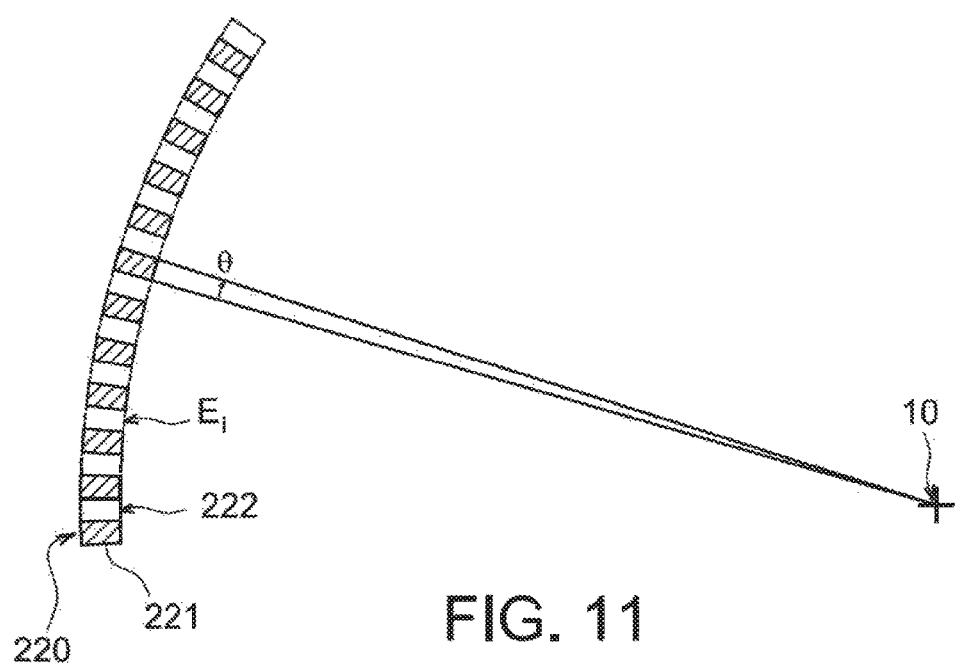
FIG. 11 illustrates an exemplary device in which the blocker includes transparent zones and opaque zones distributed on a bent portion.

Another embodiment of the imaging system illustrated in FIG. 11 provides a movement of the blocker 220 from a first position to a second complementary position by rotation, at a rotation angle θ with respect to an axis passing through the focus of the X-ray source 10, wherein θ can be proportional to the width of an opaque zone 222.

For this alternative embodiment, the blocker 20 can have a curved longitudinal cross-section or a curved profile. In this case, the opaque zones 221 and transparent zones 22 of the blocking element can have a rectangular or trapezoidal shape and be alternately distributed along a curved surface.

In the example of FIG. 11, locations Ei occupied by the transparent zones 221 in a first position of the blocker 220 are intended to be occupied by opaque zones 222 in a second position of the blocker 220 after rotation at the angle.

The curved profile is preferably such that the opaque 221 and transparent 222 zones of the blocker 20 are distributed on a sphere portion and advantageously have a checkerboard arrangement.

With such a configuration and such a movement of the blocker 20, it can be provided that a location occupied in the first position by an opaque zone 221 is occupied in the second position by a transparent zone 222 and vice versa, a location occupied in the first position by a transparent zone 222 is occupied in the first position by an opaque zone 222. The rotation amplitude to switch from the first to the second position can be in the order of the dimension of an opaque zone 221 or a transparent zone 222.

Thus, a complementarity of both image frames obtained can be achieved in order to form a full image and without an artefact of an object being examined.

Alternatively to either of the previously set forth examples, it can also be provided to integrate a blocker within an imaging system in which the source and/or the detector move(s) with respect to the object the image of which is desired to be acquired.

For example, a blocker such as that previously described in connection with FIG. 11 can be provided in an imaging system by tomosynthesis in which the X-ray source travels along an arc of circle whereas the detector remains stationary. Such a system can thereby be applied in particular to digital mammography.

According to another example, an imaging system is provided with a blocker in which the X-ray source travels along an arc of circle whereas the detector also makes an arc of circle trajectory.

Another exemplary embodiment can provide to integrate the blocker in an imaging system including an X-ray source intended to travel along an arc of circle whereas the detector is translationally moved.

Another exemplary embodiment can provide to integrate the blocker within an imaging system in which the X-ray source is translationally moved whereas the detector is also translationally moved.

As previously described, the movable blocker formed by alternate X-ray opaque zones and transparent zones can be used to perform a correction of the scattered radiation in an image.

The positioning of the blocker may also have to be determined with respect to the detector in order to know very accurately the source-detector distance and thus be able to perform a calibration of the imaging system.

A calibration can turn out to be necessary in particular in a 3D imaging system where the source-detector distance is likely to vary.

Figure 12:
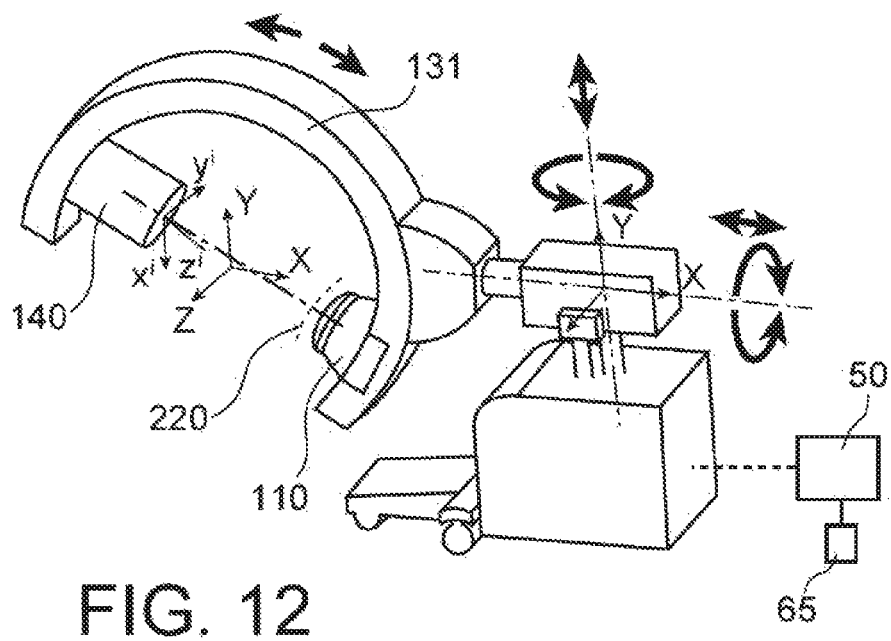
FIG. 12 illustrates an exemplary C-arm type X-ray planar imaging system, provided with a blocking element and in which the image processing module is configured to determine a position between the source and the detector by means of analysing at least one image of the blocker.

FIG. 12 illustrates an X-ray imaging system provided with a C-arm device in which the X-ray source 110 is connected to the detector 140 via an arch or C-shape arm 131.

The source 110 and the detector 140 are intended to rotate about a target object, here a patient, to make projections at several viewing angles. These projections are then exploited by the processing unit 50 coupled to the detector 140.

In this example, the processing unit 50 is further configured to implement a reconstruction algorithm in order to obtain a 3D or volume image, representing several cross-sections of the imaged object. The blocker 220 can be of the type previously described in connection with FIG. 11 provided with opaque zones and transparent zones distributed on a sphere portion.

In this type of system employed for example in operating suites, information about the relative positioning of the source 110 and the detector 140 is used in order to construct 3D tomographic images. Indeed, in the input data of the reconstruction algorithm used by the image processing unit 50 to produce 3D images, the position of the C-arm device relative to the imaged object as well as the relative position of the source 110 and the detector 140 are included. But, possible mechanical defects as well as the effect of gravity tend to modify the distance between the source 110 and the detector 140. Thereby, it can be provided to perform a calibration in order to be able to know this information for each projection made.

It is worthy of note that, to perform an image processing as previously described in connection with FIG. 9 and aiming at making a correction of the scattered radiation, the acquisition of two real images of a target object can be made in two different positions of the blocker. Two reference images $Im\_q_1$, $Im\_q_2$, different in these two different positions of the blocker can also be used.

A reference image is made without the presence of a target object between the blocker and the detector. This image thus contains only patterns of elements of the blocker.

To perform this time a calibration of an imaging system for example of the type illustrated in FIG. 12 and accurately know the source-detector distance, a single real image acquisition called "alignment image" can be sufficient and a reference image $Im\_q_1$ or $Im\_q_2$ is further used in a same position of the blocker as that assumed to make the acquisition of the alignment image.

In order to improve the calibration accuracy, at least one first reference image $Im\_q_1$, and at least one second reference image $Im\_q_2$ respectively taken in a first and a second position of the blocker 220 can however be used and a first and a second alignment image respectively in the first and the second position of the blocker with respect to the source can be acquired.

These positions of the blocker with respect to the source can be determined in the factory upon manufacturing the device, such that the distance between the source 110 and the blocker 220 is known for each of these positions.

The movement of the blocker 220 in both these positions is made with a very good repeatability. Given the good repeatability of positioning of the blocker 220 with respect to the source, a calibration to determine the source-blocker distance will be only made very rarely, for example during a maintenance operation of the imaging system. The position of the blocker with respect to the source is thus considered as being known when it is attempted to determine the position of the detector with respect to the source.

The method of determining the positioning of the detector 140 with respect to the source 110 can comprise steps of:

disposing the blocker 220 between the source 110 and the detector 140, generating a radiographic image called an "alignment" image including projected patterns of the elements of the blocker, in particular of its opaque and transparent zones in a radiographic image called an alignment image, calculating a position of the detector 140 from the coordinates of the projected patterns.

Further, prior to the step of generating the alignment image, a reference radiographic image $Im\_q1$ and/or $Im\_q2$ can have been generated so as to be able to identify the geometric transformations enabling the coordinates of elements of the blocker to be related to the coordinates of the projected patterns of the elements of the blocker in the alignment image.

Figure 13:
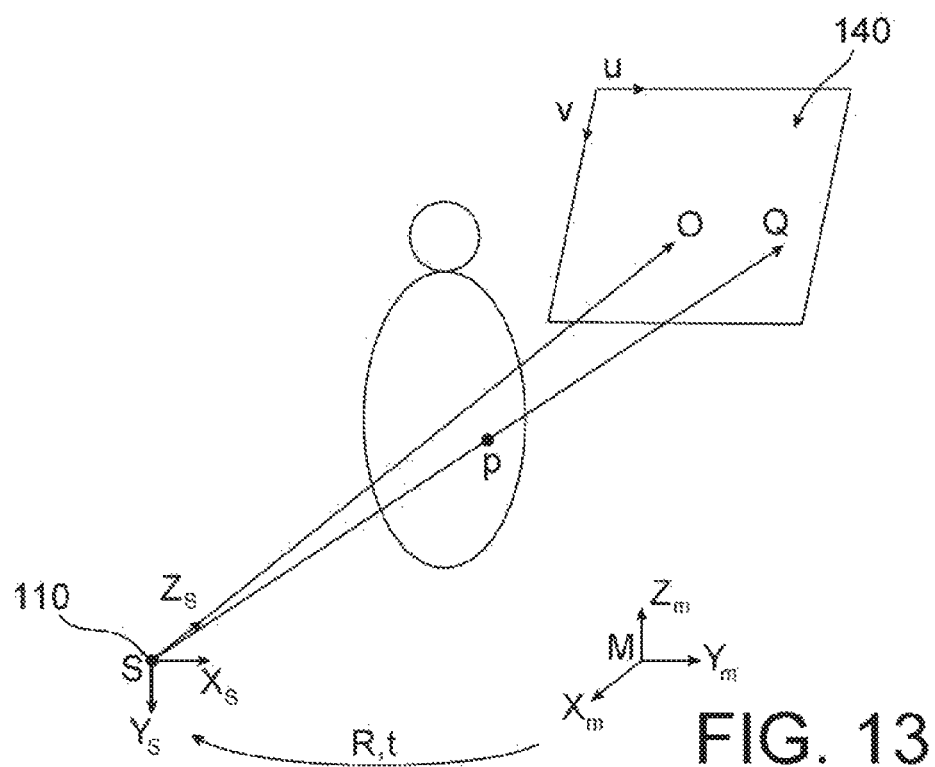
FIG. 13 illustrates an exemplary modelling of reference frames implemented by the image processing module to determine a position between the source and the detector.

FIG. 13 is now referred to on which the source detector system is modelled.

To perform this modelling, the processing unit 50 uses different reference frames, including a reference frame called a world reference frame the centre of which is a point M and in which the coordinates of a point P are expressed for example in meters.

A source reference frame the centre S of which is the X-radiation source 110 is provided with a first axis parallel to a vector u, itself parallel to the image plane of the detector 140. The source reference frame is defined by a second axis parallel to another vector v itself parallel to the image plane. A third axis of the source reference frame is as for it normal to the image plane. The coordinates of a point expressed in the source reference frame can be expressed for example in meters.

An image reference frame is also defined using vectors (u, v) having a direction parallel to the detector 140, in which the unit of the reference frame is the pixel.

A point O, called "a main point" and which corresponds to an orthogonal projection of the origin S of the source reference frame onto the detector 140 is also defined. The distance SO is then noted f and is called the focal length. The point O has (u0, v0) as coordinates in the image reference frame, the straight line SO being called the main axis.

The projection of a point P of an object onto an image plane is then a point Q expressed by a combination of geometric transformations.

The coordinates of the point P are expressed in the world reference frame and are converted into the reference frame of the source: these are extrinsic parameters.

The point P of the imaged object is then projected onto the image plane (u, v) at the point Q depending on inner characteristics of the source-detector system: these are intrinsic parameters.

In the world reference frame, the coordinates of P are: (X, Y, Z)

In the source reference frame, the coordinates of P are: (Xs, Ys, Zs)

Thus, there is the relationship:

$$\begin{bmatrix} X_s \\ Y_s \\ Z_s \end{bmatrix} = R \begin{bmatrix} X \\ Y \\ Z \end{bmatrix} + t = [R \mid t] \begin{bmatrix} X \\ Y \\ Z \end{bmatrix}$$

R, t are respectively a rotation operation and a translation operation making it possible to switch from the world reference frame to the source reference frame.

The rotation operation R can be expressed as the product of 3 rotation matrices, each matrix representing a rotation about an axis of the reference frame.

The coordinates (x, y, z) in the source reference frame of the projected Q into the image plane of the point P can be expressed in the following way using the Thales relationship:

$$\begin{bmatrix} x \\ y \\ z \end{bmatrix} = \begin{bmatrix} f/Z_s & 0 & 0 \\ 0 & f/Z_s & 0 \\ 0 & 0 & f/Z_s \end{bmatrix} \begin{bmatrix} X_s \\ Y_s \\ Z_s \end{bmatrix}$$

The coordinates (u, v) of the projected Q in the image reference frame can be expressed by the following relationship:

$$\begin{bmatrix} u \\ v \end{bmatrix} = \begin{bmatrix} k_u & 0 & u_0 \\ 0 & k_v & v_0 \end{bmatrix} \begin{bmatrix} x \\ y \\ 1 \end{bmatrix}$$

with ku and kv conversion factors for example of meters into pixels the value of which depends on the detector type. When the pixels of the detector 140 are square, there is ku=kv=k. This expression means that the centre of the image reference frame (u, v) is in a corner of the image and that an offset of u0 and v0 is applied to express the coordinates with respect to this centre.

Consequently, the following relationship between Q (u, v) and P (Xs, Ys, Zs) is obtained:

$$\begin{bmatrix} au \\ av \\ a \end{bmatrix} = \begin{bmatrix} k \times f & 0 & u_0 \\ 0 & k \times f & v_0 \\ 0 & 0 & 1 \end{bmatrix} \begin{bmatrix} X_s \\ Y_s \\ Z_s \end{bmatrix} = K \begin{bmatrix} X_s \\ Y_s \\ Z_s \end{bmatrix}$$

K is a first geometric transformation matrix representative of intrinsic parameters of the source-detector system: kf, u0 and v0.

Thus, the relationship between a point P of an object to be imaged expressed in the world reference frame and its projected Q into the image plane is:

$$Q = K \times P$$

To determine the position of the detector 140 with respect to the source 110, the processing unit 50 implements a detection of projected patterns of the blocker 220 into at least one image.

In the case of an imaging system of the type of FIG. 12, the distance between the source 110 and the blocker 220 is considered as being known. The world reference frame is as for it placed at the source 110.

The processing unit 50 can be configured to determine the position of the detector 140 from a reference position of the detector 140.

For this reference position, a reference matrix Kref with the intrinsic parameters, i.e. f, $u_0$, $v_0$, are saved in a memory 55 exploitable by the processing unit 50.

The reference matrix Kref corresponds to a matrix representative of a geometric transformation relating coordinates of projected patterns of elements (opaque and/or transparent zones) of the blocker 220 into a reference image Im_q1 or Im_q2 taken when the system is in the reference position with those of the elements of the blocker 220 in the reference position.

The blocker 220 is then at a known distance from the detector 140, the detector 140 being at a reference distance from the source 110. The presence of an object other than the blocker 220 is not necessary to acquire this reference image. Thus the reference image Imq1 or Im_q2 is acquired without the presence of a target object between the blocker and the detector.

The image processing unit 50 thus knows the coordinates of patterns of the blocker 220 in the reference image Im_q1 or Im_q2 taken when the system is in the reference position and knows a correspondence between these coordinates and those of the elements of the blocker 220 in the world reference frame.

The data related to the reference position can be input by the imaging system manufacturer itself. These data are then stored in the memory 55 coupled to the processing unit 50.

Then, a real position of the plane of the detector 140 desired to be determined is then considered. An acquisition of an image Im_al called "alignment image" is then performed. This time, in addition to the presence of the blocker 220, a target object to be investigated desired to be imaged can be present between the source 110 and the detector 140.

The real position of the detector 140 is then expressed in a reference frame S2 of the source 110 for a second view. For this real position, the intrinsic parameters are described by a Kali matrix.

To acquire the real image, the position of the blocker 220 with respect to the source remains unchanged with respect to that upon acquiring a corresponding reference image. In other words, in a case where the blocker 220 is in the first position with respect to the source to acquire the real image, the corresponding reference image Im_q1 used to determine the position of the detector is an image taken when the blocker 220 is in the same first position. In another case where the blocker 220 is in the second position to acquire a real image, the corresponding reference image Im_q2 is an image taken when the blocker 220 is in the same second position.

A mathematical operation relating the patterns of the blocker 220 in the real position to the patterns of the blocker of the reference position is defined. This operation is a planar homography. Such a type of operation is defined for example in document "On-line C-arm Intrinsic Calibration: Simulation Study", by B. Spencer & L. Desbat, IEEE Medical imaging conference 2014. The processing unit 50 thus calculates the parameters of a second matrix H of geometric transformation relating this time coordinates of projected patterns of elements (opaque and/or transparent zones) of the blocker 220 in the reference image Im_q1 or Im_q2 taken when the system is in the real position with those of the elements of the blocker 220 in the reference position.

The processing unit 50 can use a general relationship enabling the homography H to be expressed as a function of rotation and translation operations making it possible to switch from the source reference frame S1 in the first view corresponding to the reference image to the source reference frame S2 in the second view corresponding to the alignment image.

If the world reference frame is attached to the source 110, only a rotation matrix R relating both source reference frames S1 and S2 can be considered.

In this case, there is no translation, which results in a translation matrix t such that t=0. The homography H and the rotation matrix R are then related by the following formula:

$$HK_{ref} = K_{ali}R$$

Kref is known and H is calculated by the processing unit 50 from the matches between the elements of the blocker and the projected patterns.

$HK_{ref}$ can be decomposed into 4 matrices: a first matrix in the form of a matrix of intrinsic parameters which will represent the Kali matrix and three other matrices which will represent the rotations with respect to the 3 axes of the reference frame S1.

These three matrices represent the overall rotation which makes it possible to switch from the reference frame S1 to the reference frame S2. These are the matrices R and Kali which inform about the position of the detector 140 when the system is acquiring image. The processing unit 50 then calculates the distance between source 110 and detector 140 using these matrices.

It may be sufficient for the processing unit 50 to have 4 points that one is able to match in both reference and real positions to calculate the planar homography H.

A higher number of points can however be used.

A processing such as described above to enable the real position of the detector to be determined comprises prior to determining coordinates of projected patterns, detecting projected patterns of the blocker 220 in an image, in particular in the alignment image Im_al or in the reference image Imq1 or Im_q2, the processing unit 50 can be configured to perform an edge detection. This detection is for example made by means of operators of the Canny filter type.

The processing unit 50 can also be configured so as to detect characteristics of patterns of the blocker 220 in an image, in particular in the alignment image or in the reference image. Characteristics such as geometric parameters of straight line segments: straight line equation, coordinates of end points of segment and of intersection points of lines can then also be obtained. Such a detection can be made for example using a Hough transform.

In the case, for example, where the blocker 220 has an arrangement of its opaque zones of the type illustrated in FIG. 10, a detection of a checkerboard pattern is implemented. In another case, for example, where the blocker is of the type illustrated in FIG. 2, a detection of a pattern in the form of parallel strips is performed. Because of alternate radio-transparent and radio-opaque zones, a pattern of the blocker 220 in the image is particularly contrasted, which enable the edges of the patterns of the blocker 220 to be very accurately detected and consequently an increased detection fineness of the position of the detector 140 with respect to the source 110 to be obtained.

The image processing unit 50 is configured to match projected patterns identified with the elements of the blocker 220, that is its opaque and/or transparent zones the arrangement of which is known. This can be made using a characteristic table stored in the memory 55 coupled to the processing unit 50. For example, the table comprises the characteristics of the elements (opaque and/or transparent zones) of the blocker 220, namely their shape, length and position in the blocker 50. More particularly, the matching consists for the processing unit 50 in scanning the alignment image to identify projected patterns and for each projected pattern identified, in calculating the characteristics of the pattern. Then, the processing unit 50 compares the calculated characteristics with those of the table and locates the element of the blocker which corresponds to the projected pattern.

To map patterns between a reference image Imq1 and/or Imq2 and an image taken during a test using the system as illustrated in FIG. 12, a so-called "small movements" criterion. Indeed, the mechanical inaccuracies of the C-arm device are in the order of a few mm or degrees.

Thereby, it is known that the offset of patterns is small which makes it possible to have a similarity criterion based on the spatial proximity. A method to perform the matching of reference points to real points of measurements is for example given in document "Two Dimensional Projective Point Matching", Phd Thesis of Jason Denton, Colorado State University (2002).

The use of a radiopaque blocker at several positions enables an accurate calibration of the imaging system to be performed. Once this calibration is performed and the source-detector distance properly determined, a radiographic image can be obtained which can then be corrected using an image processing such as previously described in connection with FIG. 9 and which enables the contribution in the image of the scattered radiation to be corrected. The blocker 220 does not disturb the final image but on the contrary, enables it to be improved.

What is claimed is:

1. An X-ray imaging system comprising:
   an X-ray source,
   an X-ray detector,
   a blocker formed alternately by one or more opaque zones enabling X-rays to be blocked and one or more transparent zones enabling X-rays to pass therethrough,
   blocker moving means configured to move the blocker between at least one first position and at least one second position, such that in the first position, an opaque zone fully occupies a first given location and a transparent zone fully occupies a second given location, in the second position, the first given location is fully occupied by a transparent zone, the second given location being fully occupied by an opaque zone,
   image acquiring means configured to perform a first acquisition of a first image when the blocker is in the first position and to perform a second acquisition of a second image when the blocker is in the second position,
   an image processing unit configured to determine a position of the detector from coordinates of one or more projected patterns of the blocker in the first image and/or in the second image.

2. The X-ray imaging system according to claim 1, wherein the processing unit is further configured to:
   deduce from a relative position of the detector with respect to the blocker that a given pixel of the detector belongs to a first pixel category or to a second pixel category,
   estimate the primary radiation of the given pixel of the detector using a first estimator $\hat{P}$ when the given pixel belongs to the first category or using a second estimator $\hat{P}'$ when the given pixel belongs to the second category.

3. The X-ray imaging system according to claim 2, wherein the processing unit is further configured to estimate the primary radiation received by a given pixel n of the detector using an estimator $\hat{P}$, depending on a ratio between:
   a difference $I_1(n)-I_2(n)$ between a radiation intensity $I_1(n)$ detected by the given pixel n during the first acquisition and a radiation intensity $I_2(n)$ detected by the pixel n during the second acquisition,
   a difference $q_1(n)-q_2(n)$, with $q_1(n)$, $q_2(n)$ being predetermined parameters representative of primary radiation fractions received by the pixel n of the detector in the first position of the blocker and in the second position of the blocker without a target object.

4. The X-ray imaging system according to claim 1, wherein the processing unit estimates the primary radiation received by a given pixel m of the detector using an estimator $\hat{P}'$, the estimation $\hat{P}'(m)$ of the primary radiation received by a given pixel m, being a function of a primary radiation intensity $I_1(m)$ detected by the given pixel m during the first acquisition of an intensity $I_2(m)$ detected by the pixel m during the second acquisition, and of $\hat{S}int(m)$ a value estimated by interpolating the scattered radiation of the pixel n from a scattered radiation value calculated for its neighbouring pixels.

5. The imaging system according to claim 1, wherein the movement of the blocker is a translation of the blocker by a given pitch p and in a plane parallel to the detector.

6. The imaging system according to claim 1, wherein the opaque zones and the transparent zones of the blocker have a width l, the translation pitch p being equal to k*l, with k being an integer.

7. The imaging system according to claim 1, wherein the blocking element includes a front face on which the opaque zones and the transparent zones are distributed as parallel strips or in the form of a checkerboard arrangement.

8. The imaging system according to claim 1, wherein the opaque zones (21a) are provided with longitudinal faces tilted with respect to each other and along directions that converge to the X-ray source.

9. The imaging system according to claim 1, wherein the movement is a rotation of the blocker (220) about an axis passing through the X-ray source.

10. The imaging system according to claim 9, wherein the opaque zones and the transparent zones of the blocker are distributed on a curved surface.

11. The imaging system according to claim 1, wherein the image processing unit includes:
   a memory for storing parameters of a first geometric transformation matrix relating coordinates of reference patterns with the coordinates of elements of the blocker respectively, each reference pattern corresponding to a projection of an element of the blocker in a reference radiographic image ($Im\_q_i$, $Im\_q_2$) generated when the detector is located at a reference distance from the source without a target object between the blocker and the detector, the blocker being then in a given position from said first and second positions,
   the image processing unit being further configured to:
   identify projected patterns of elements of the blocker in another radiographic image called an alignment radiographic image generated when the blocker is in the given position with respect to the detector, and to match the projected patterns in the alignment image with respectively elements of the blocker, calculate parameters of a second geometric transformation matrix relating the coordinates of the patterns projected in the alignment radiographic image with the coordinates of the reference patterns, and calculate the position of the detector from the parameters of the first and second matrices.

12. A method for calibrating a radiographic imaging system according to claim 1, comprising the following steps of:
   disposing the blocker between the source and the detector,
   acquiring by the detector at least one alignment radiographic image including one or more projected patterns of the blocker,
   determining coordinates of the projected patterns of the blocker in the alignment image and
   calculating a position of the detector from coordinates of the projected patterns in the alignment image.

* * * * *